(12) United States Patent
Gerlach et al.

(10) Patent No.: US 7,422,570 B2
(45) Date of Patent: Sep. 9, 2008

(54) SYRINGE PUMP HAVING A PISTON BRAKE

(75) Inventors: Hans-Josef Gerlach, Marsberg (DE); Rene Wildner, Melsungen (DE); Berthold Wolfram, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 914 days.

(21) Appl. No.: 10/346,609

(22) Filed: Jan. 17, 2003

(65) Prior Publication Data
US 2003/0149402 A1 Aug. 7, 2003

(30) Foreign Application Priority Data
Jan. 22, 2002 (DE) .............................. 202 00 885 U

(51) Int. Cl.
*A61M 37/00* (2006.01)
(52) U.S. Cl. .................... 604/154; 604/131; 604/155
(58) Field of Classification Search ................ 604/118, 604/121, 131, 151, 152, 154, 155
See application file for complete search history.

(56) References Cited

U.S. PATENT DOCUMENTS

| | | | | |
|---|---|---|---|---|
| 4,191,187 A | * | 3/1980 | Wright ....................... | 604/155 |
| 4,804,368 A | * | 2/1989 | Skakoon et al. ............. | 604/155 |
| 4,988,337 A | * | 1/1991 | Ito .............................. | 604/154 |
| 5,176,646 A | * | 1/1993 | Kuroda ........................ | 604/154 |
| 6,592,551 B1 | * | 7/2003 | Cobb .......................... | 604/155 |

FOREIGN PATENT DOCUMENTS

| | | | |
|---|---|---|---|
| EP | 0 402 553 A1 | | 12/1990 |
| EP | 0 566 825 A1 | | 10/1993 |
| EP | 0566825 A1 | * | 10/1993 |
| EP | 1 195172 A2 | | 4/2002 |
| JP | 10216229 A | | 8/1998 |

* cited by examiner

*Primary Examiner*—Kevin C. Sirmons
*Assistant Examiner*—Bhisma Mehta
(74) *Attorney, Agent, or Firm*—Klein, O'Neill & Singh LLP

(57) ABSTRACT

The syringe pump comprises a receiving position for a syringe. The piston plate of the syringe is moved by a drive head which is fastened to a drive rod. For locking the piston rod prior to fixing the piston plate in the drive head, a braking element is provided on a syringe holding head. The syringe holding head further serves for determining the respective syringe size. After placing the syringe holding head against a syringe cylinder, the brake element is actuated to temporarily engage the piston rod and fix it relatively to the syringe cylinder.

17 Claims, 5 Drawing Sheets

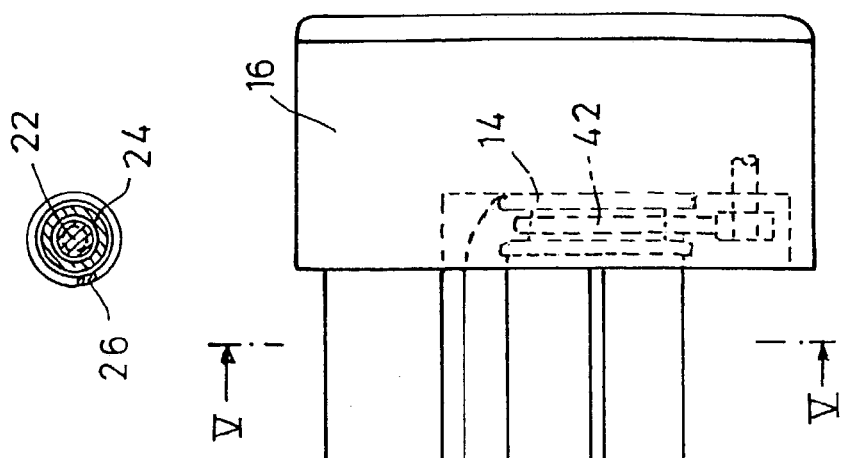
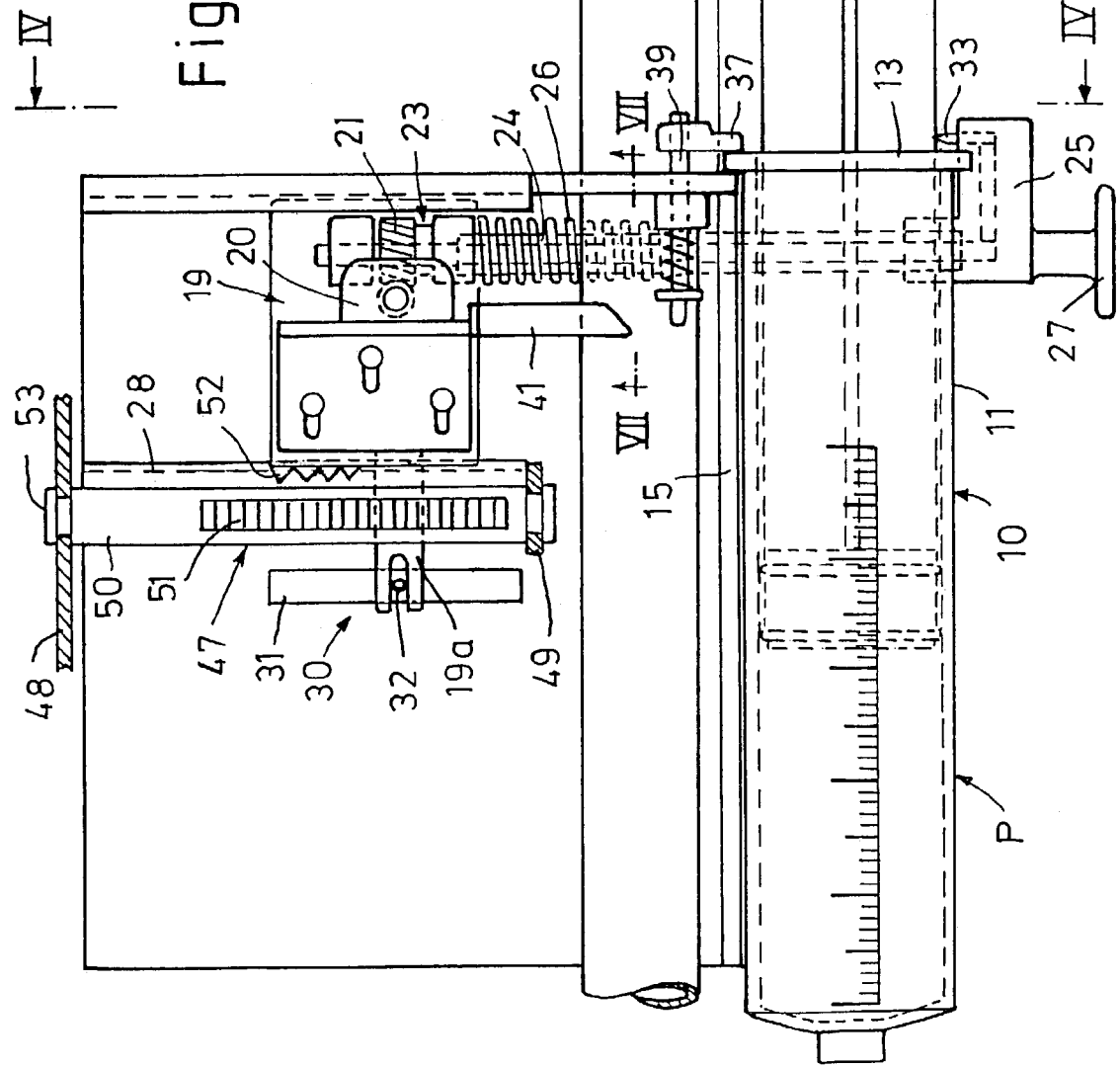

SYRINGE PUMP HAVING A PISTON BRAKE

CROSS-REFERENCE TO RELATED APPLICATION

This application claims priority from German Patent Application No. 202 00 885.1, titled A SYRINGE PUMP HAVING A PISTON BRAKE, filed in Germany on Jan. 22, 2002, the entire contents of which is incorporated by reference herein as though set forth in full.

BACKGROUND OF THE INVENTION

The present invention relates to a syringe pump having a piston brake for controlled discharge of medical syringes.

From EP 0 566 825 A1 a syringe pump having a piston brake is known, which comprises a first holder for fixing the cylinder of a syringe and a linearly movable second holder for displacing the piston rod of the syringe.

A stationary piston brake engages the piston rod and, when the piston cylinder is inserted, blocks the piston rod until the piston rod has been gripped by the second holder. Thereby unintentional displacement of the piston rod caused by suction effect or mechanical movement prior to the start of infusion is prevented. Securing the piston rod after an exchange of syringes is of importance in particular for small syringes having small frictional forces.

Further, syringe pumps are known which allow an automatic exchange of syringes. For this purpose, a syringe holding head is provided which, after insertion of a syringe, scans said syringe and determines the syringe size. On the basis of the syringe size the displacement velocity and other parameters are automatically adjusted.

SUMMARY OF THE INVENTION

It is an object of the invention to provide a syringe pump having a piston brake, which, in the syringe position, requires only a simplified support.

In the syringe pump according to the invention the brake element is arranged on the syringe-position side opposite the drive rod, i.e., on the outside. The brake element is movable toward a syringe bearing arranged on the drive-rod side in order to impart the brake effect. Consequently, the syringe bearing is located on the drive-rod side which defines the inside. Against this syringe bearing syringes of various sizes may be placed for assuming a defined position suitable for the discharge process.

According to a preferred aspect of the present invention, the brake element is provided on a syringe holding head which is movable transversely to a syringe in the syringe position. Such a syringe holding head normally engages only the syringe cylinder. It serves as a holder which secures the syringe cylinder against displacement out of the syringe position. According to the invention, this syringe holding head is additionally provided with a brake element which acts upon the piston rod projecting out of the syringe cylinder. One advantage of this measure is that the piston brake is spatially related to the syringe cylinder, i.e., activation and deactivation of the piston brake require only a very small amount of displacement of the brake element. After closing of the syringe holding head and recognition of a proper syringe, the piston brake automatically imparts a braking effect until the motorized drive head has recognized and locked the piston plate of the syringe. Thereafter, the piston brake is released by displacing the brake element, wherein engagement of the syringe holding head with the syringe cylinder is however not released.

According to a preferred embodiment of the present invention, a linear drive for the brake element extends below the syringe position, wherein a motor is arranged on one side and the syringe holding head on the other side of the drive rod. The linear drive effects adjustment of the brake element from the drive-rod side, wherein the syringe is pulled against the syringe bearing which is also located on the drive-rod side.

Preferably, the brake element is provided on a syringe holding head, wherein a portion of the syringe holding head engages the syringe cylinder, and the brake element engages the piston rod. In this manner, the functions of syringe holding head and brake element can be combined in one unit.

According to a preferred aspect of the present invention, an actuating means for the brake element is arranged on a slide which is connected with the syringe holding head, and a sensor detecting the position of the slide is provided for the purpose of determining the syringe size. When the syringe holding head is manually removed to allow the syringe to be inserted, and is then placed against the syringe, the slide carrying the actuating means for the brake element moves together with the syringe holding head. When the syringe is in the syringe position, the sensor provides a position signal indicative of the syringe holding head position and thus the size (diameter) of the inserted syringe.

Preferably, the slide is connected via a tube with the syringe holding head, through which tube extends an axially movable rod for adjusting the brake element relatively to the syringe holding head. This configuration offers a particularly simple mechanism for adjusting the brake element relatively to the syringe holding head.

To definedly position the syringe in axial direction when the syringe is inserted into the syringe pump, a positioning means engaging a winglike syringe portion is provided according to a preferred aspect of the present invention, said positioning means being coupled with the syringe holding head such that it presses the winglike syringe portion axially against a stop wall when the syringe holding head radially approaches an inserted syringe.

The invention further relates to another embodiment of the syringe pump. Here, the brake element defining the piston brake is provided on a syringe holding head which radially presses the syringe cylinder against a syringe bearing.

BRIEF DESCRIPTION OF THE DRAWINGS

Hereunder an embodiment of the present invention is explained in detail with reference to the drawings in which:

FIG. 3 shows, in a similar representation as that of FIG. 1, the condition with properly inserted syringe and closed syringe holding head;

FIG. 7 shows a section along line VII-VII of FIG. 3; and

DETAILED DESCRIPTION OF THE INVENTION

Figure 1:
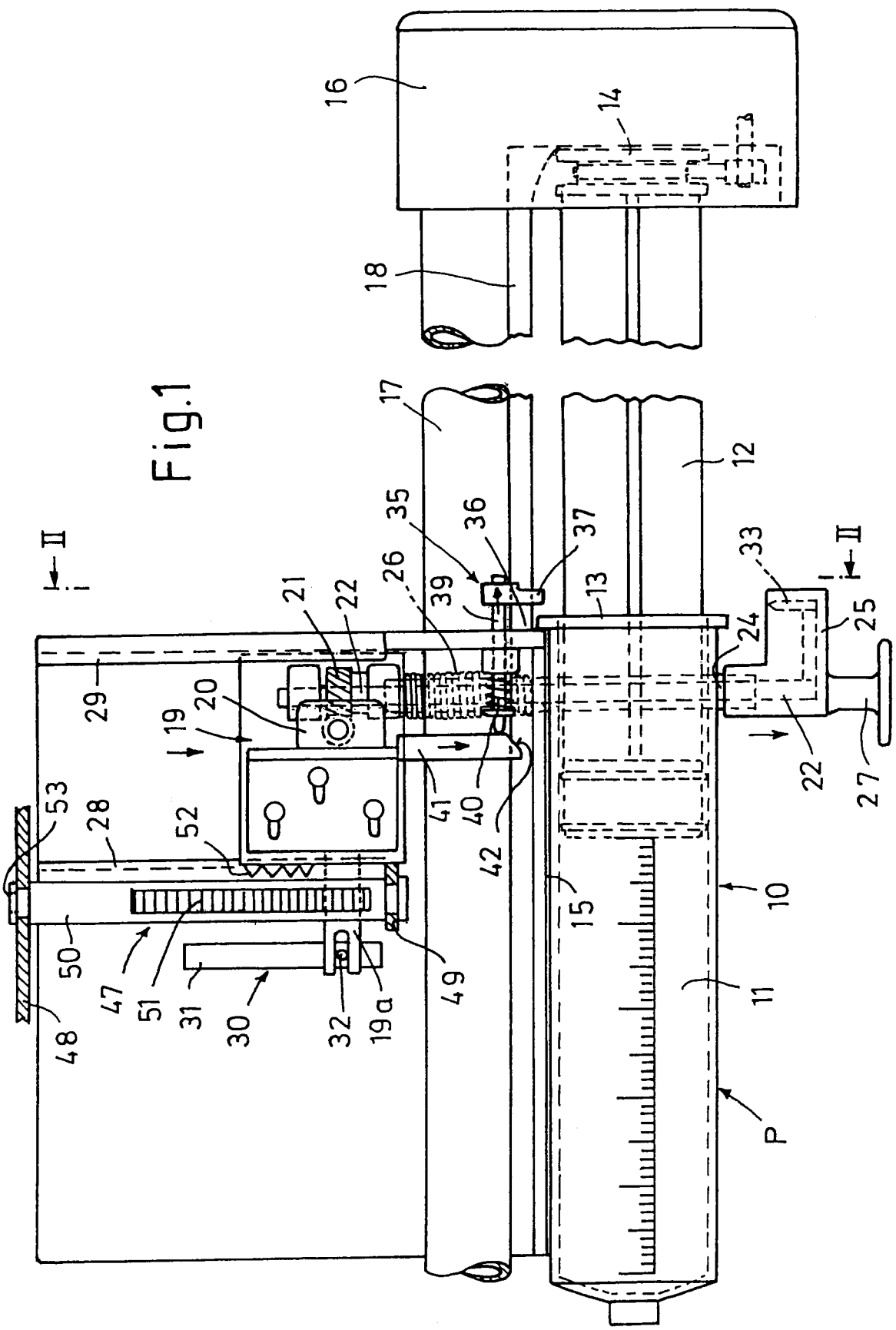
FIG. 1 shows a plan view of a syringe pump with removed syringe holding head and with the locking means in the release position.
Figure 2:
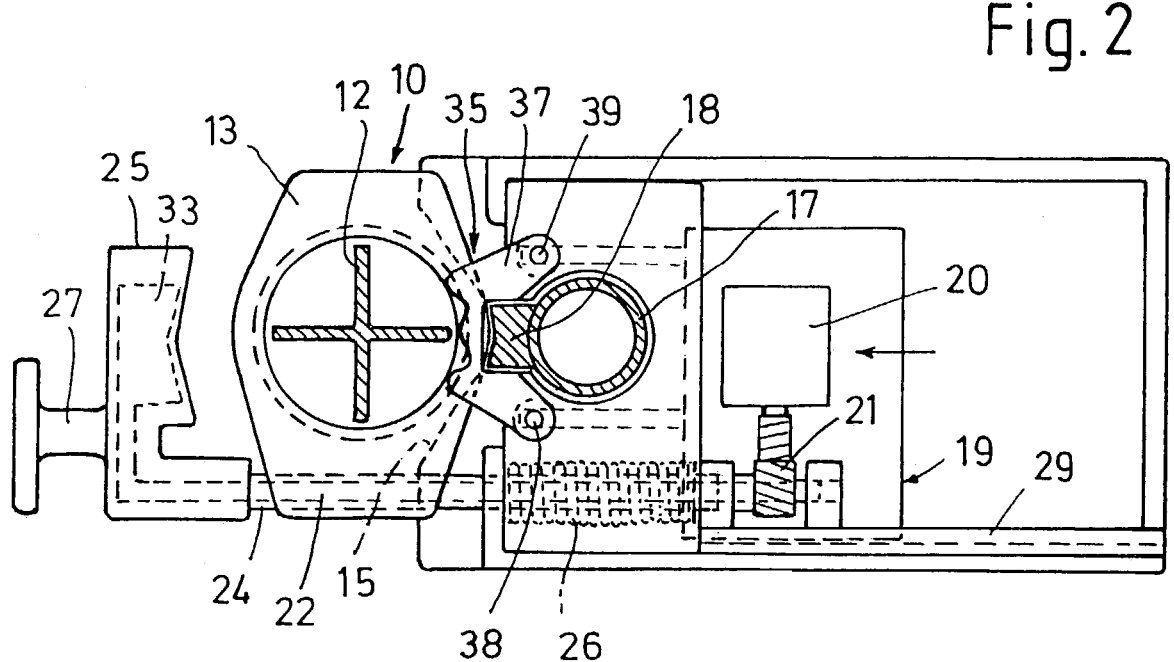
FIG. 2 shows a section along line II-II of FIG. 1.
Figure 4:
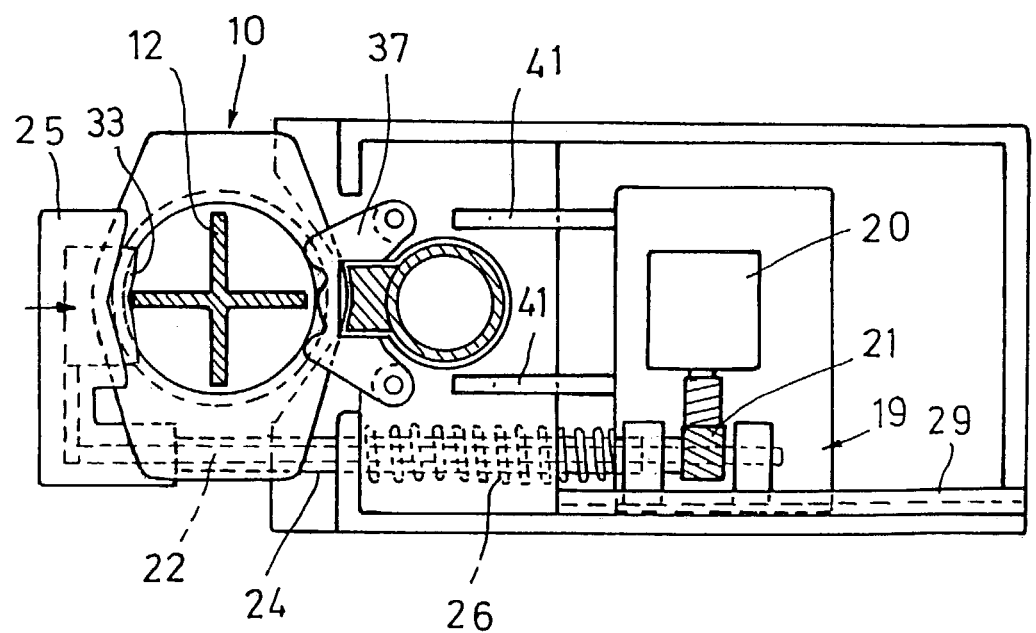
FIG. 4 shows a section along line IV-IV of FIG. 3.
Figure 5:
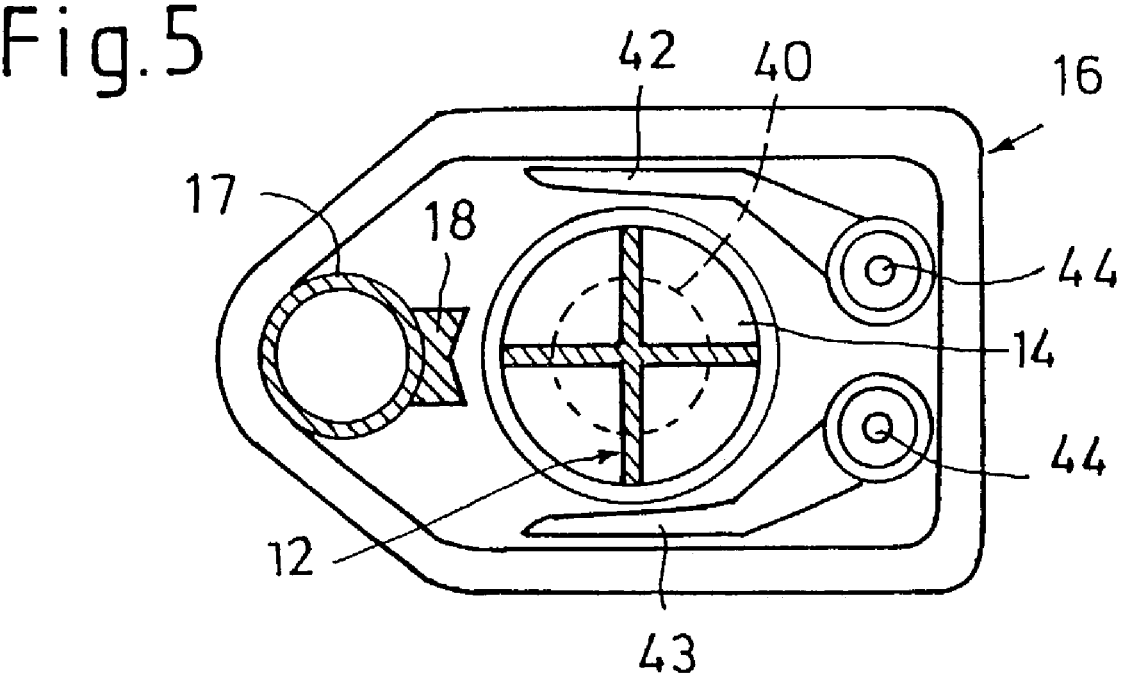
FIG. 5 shows a section along line V-V of FIG. 3 with open arms of the drive head.
Figure 6:
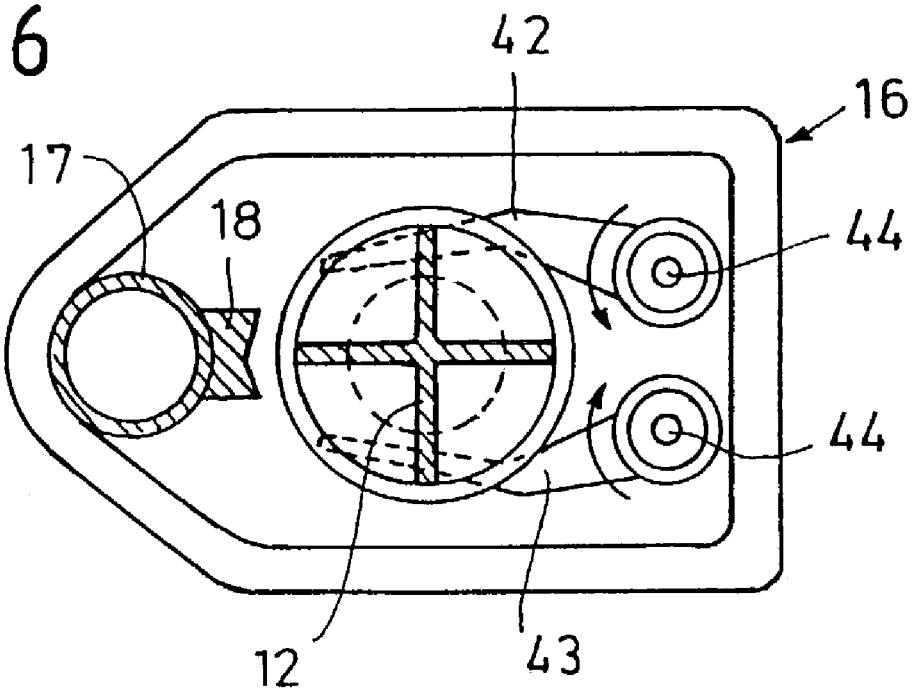
FIG. 6 shows the drive head of FIG. 5, wherein the arms are locked with the piston rod.

The syringe pump is generally configured like that described in EP 0 566 825 A1 such that a general description of the overall device is omitted here. (EP 0 566 825 A1 was published on Oct. 27, 1993 and is incorporated in its entirety by this reference.)

The syringe pump serves for discharging a syringe 10 which comprises a syringe cylinder 11 and a piston rod 12.

The syringe cylinder 11 is provided at its open end with a projecting winglike syringe portion 13, and the piston rod comprises at its end a piston plate 14. The piston rod 12 has a cruciform profile made from ribs arranged perpendicularly to each other.

In the syringe position P the syringe 10 is placed against a laterally arranged syringe bearing 15 in such a manner that the winglike syringe portion 13 assumes a specified axial position. In this condition, the piston rod 12 is retracted from the syringe cylinder 11, and the syringe cylinder 11 is filled with a liquid.

For moving the piston rod 12 a linearly movable drive head 16 is provided on the syringe pump, said drive head 16 being attached to an elongate drive rod 17. The drive head can be moved toward the piston plate 14 to receive and lock the latter. According to FIG. 3, the drive head can be moved to the left for discharging the contents of the syringe 10. On the drive rod 17 side a supporting bearing 18 is located upon which the piston plate 14 can rest when the piston brake is actuated.

On the drive rod 17 side a motor 20 having a vertical axis is arranged on a slide 19. The motor 20 drives, via a worm wheel, a helical gear wheel 21 supported on the slide 19. The gear wheel 21 is provided with a threaded bore which is in engagement with the thread of a spindle rod 22. By rotating the gear wheel 21 the spindle rod 22, which is secured against rotation, is axially displaced. Thus the spindle rod 22 defines a linear drive 23.

A tube 24 extends, transversely to the longitudinal direction of the syringe 10 and below the drive rod 17, from the slide 19, through which tube 24 the spindle rod 22 extends. On the opposite side of the syringe 10 a syringe holding head 25 is fastened to the end of the tube 24. On the tube 24 a helical spring 26 is located which is supported on the syringe bearing 15 associated with the housing of the syringe pump, and presses the slide 19 out of the syringe position. Since, on the other hand, the tube 24 is connected with the slide 19, and at the end of the tube 24 the syringe holding head 25 is located, the syringe holding head is pressed against the syringe 10 which is in the syringe position P, thus pressing the syringe against the syringe bearing 15. The syringe holding head 25 is rotatable about the axis of the tube 24. The syringe holding head 25 comprises a handle knob 27 by means of which the syringe holding head 25 can be manually pulled away from the syringe and can be rotated.

The slide 19 is guided, transversely to the longitudinal direction of the syringe 10 in the syringe position P, in guide rails 28,29. Next to this linear guide a sensor 30 configured as a potentiometer 31 is arranged. The tap 32 of the potentiometer 31 is adjusted by a slider 19a connected with the slide 19. In this manner, the electric resistance of the potentiometer 31 indicates the position of the slide 19 and thus the position of the syringe holding head 25. The signal of the sensor 30 thus provides information on the syringe size and/or the syringe diameter with closed syringe holding head 25.

The spindle rod 22 extends into the syringe holding head 25 and carries a brake element 33 which is configured as a cutting edge and arranged within the syringe holding head 25, the tip of the cutting edge facing the syringe cylinder 11. By operating the motor 20 the brake element 33 is moved between a retraction position (FIG. 1) and an active braking position (FIG. 3). In the braking position the brake element 33, which moves along the winglike syringe portion 13, engages the piston rod 12 to block any displacement of the piston rod 12 relative to the syringe cylinder 11.

The syringe pump is further provided with an axial positioning means 35 which axially presses the winglike syringe portion 13 against a stop wall 36. The positioning means 35 comprises a plate or slider 37 which is guided, on two rods 38,39, axially to the syringe 10. The slider 37 projects into the path of the winglike syringe portion 13. The slider 37 is fastened to two parallel rods 38, 39 which extend parallel to the axis of the syringe 10 and are biased, by a spring 40, toward the front, i.e., toward the outlet end of the syringe cylinder 11. The rear ends of the rods 38,39 are controlled by a control means 41 connected with the slide 19, since the control means 41 comprises an inclined surface 42 acting as a cam. When the slide 19 is moved toward the syringe position P, the control means 41 push the slider or plate 37 toward the rear, i.e., away from the stop wall 36, such that the winglike syringe portion 13 can be positioned into the space created therebetween. When the syringe holding head 25 is then released, such that it is placed against the syringe cylinder 11, the slider or plate 37 is pulled forward by the spring 40 action, thereby pressing the winglike syringe portion 13 against the stop wall 36 thus causing the syringe cylinder 11 to assume an exact axial position.

The drive head 16 contains a piston plate sensor 40 which responds to the presence of a piston plate 14 thus communicating to the device that the drive head 16 has been moved to the piston plate 14 of an inserted syringe. The piston plate sensor 40 is arranged in a recess of the drive head 16. The recess further contains controlled arms 42,43 which are pivotable about a pivot pin 44 and are movable toward each other to lock the piston plate 14 on the drive head.

For inserting a syringe 10 into the syringe pump the syringe holding head 25 is removed by pulling the handle knob 27. Simultaneously, the positioning means 35 is brought into the open position. Now the syringe cylinder 11 can be inserted. Then the syringe holding head 25 is placed from outside against the syringe cylinder 11. The spring 26 causes the syringe holding head 25 to press the syringe cylinder 11 against the syringe bearing 15. When the syringe holding head 25 is placed against the syringe cylinder 11, the plate 37 of the positioning means 35 presses the winglike syringe portion 13 against the stop wall 36. When the syringe holding head 25 is released, the syringe is exactly positioned. The sensor 30 detects, on the basis of the position assumed by the slide 19, the syringe size and provides a corresponding signal to the control means. When the advance velocity is determined, the syringe size is taken into consideration.

When the syringe holding head 25 is released, the motor 20 is put into operation such that the tip of the brake element 33 is moved out of the syringe holding head 25 and pressed against the piston rod 12. Thus the piston rod 12 is fixed relatively to the syringe cylinder 11.

Then the drive rod 17 is automatically moved such that the drive head 16 approaches the piston plate 14. When the piston sensor 40 detects that the piston plate is correctly positioned, the arms 42,43 are actuated to lock the piston plate in the drive head 16. Then the motor 20 is put into reverse to remove the brake element 33 from the piston rod 12. Now the drive head 16 can be moved to discharge the syringe 10.

Figure 8:
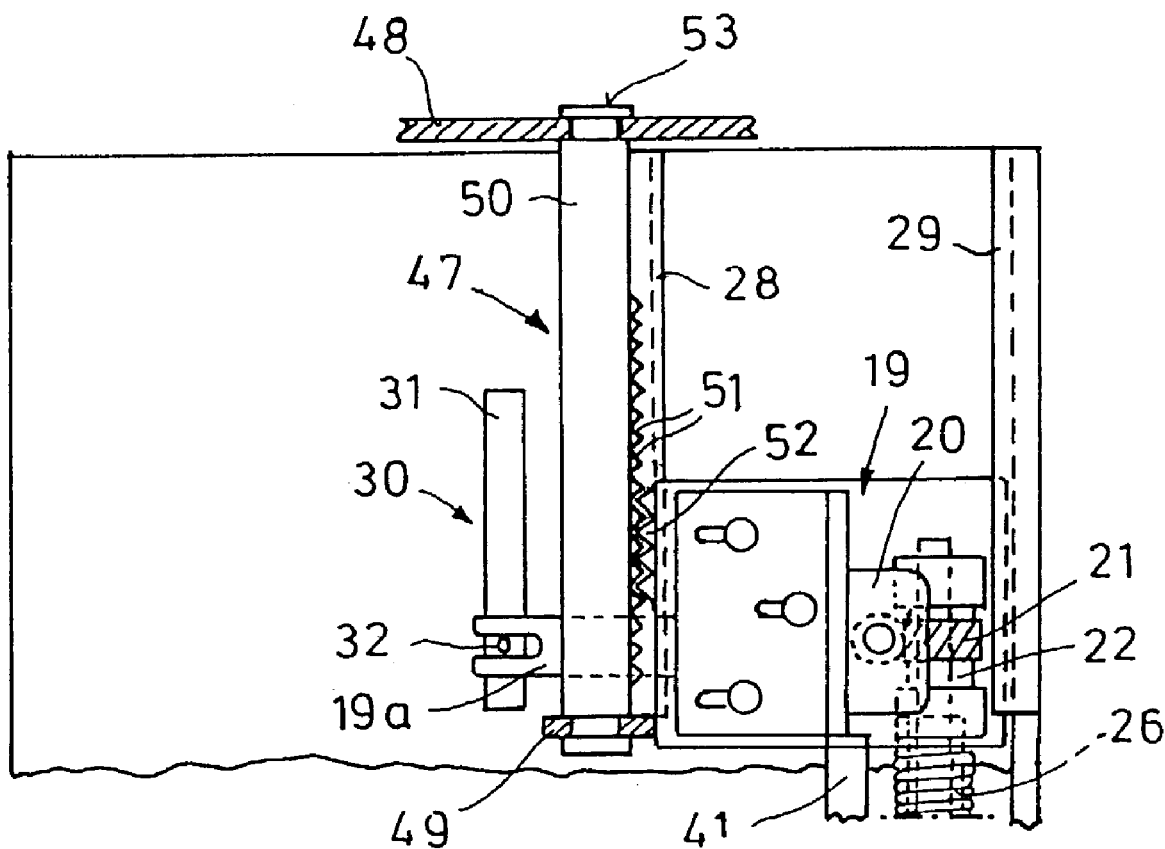
FIG. 8 shows a detail of FIG. 1, wherein the locking means for the syringe holding head is in the locking position.

It is further possible to provide a forced limitation of the movement of the slide 19 to secure the inserted syringe on the device. Such securing of the syringe can be particularly appropriate for PCA (patient-controlled analgesia). This is a kind of pain treatment. The securing prevents too high a drug dose from being administered to the patient by his/her own manipulation or manipulation of a third person. Forced limitation is effected by a locking means 47 comprising a shaft 50 which is rotatably supported, parallel to the slide 19, on housing walls 48,49, the shaft 50 having a rack-type toothing 51 on one side. Said toothing 51 can, by rotating the shaft 50, be brought into engagement with a tooth segment 52 located on the slide 19. When the toothed portions are in engagement with each other (FIG. 8), the slide 19 is blocked such that it cannot move. The shaft 50 can be rotated only with the aid of a special wrench which is inserted into a profiled opening (not shown) provided in the front wall 53.

Although a preferred embodiment of the present invention has been specifically illustrated and described herein, it is to be understood that minor variations may be made without departing from the spirit and scope of the present invention, as defined in the appended claims.

What is claimed is:

1. A syringe pump comprising a syringe holder for holding a syringe cylinder of a syringe, a syringe holding head, a device for sizing the syringe cylinder, a drive head for engaging a piston plate of a piston rod located inside the syringe, the drive head being carried by a drive rod extending parallel to the syringe on a first side of the syringe when the syringe is inserted, and a brake element, transversely movable to a longitudinal direction defined by a lengthwise direction of the syringe when the syringe is inserted,
   wherein a portion of the syringe holding head engages the syringe cylinder on a second side of the syringe opposite the drive rod on the first side; and
   wherein the brake element is provided on the syringe holding head and configured to press toward a syringe bearing arranged on the first side to move into contact with the piston rod for controlling forward movement of the piston rod.

2. The syringe pump according to claim 1, wherein the syringe holding head is configured for contacting and holding the syringe cylinder.

3. The syringe pump according to claim 2, wherein an actuating means for the brake element is arranged on a slide coupled to the syringe holding head and wherein the device for sizing is a sensor for detecting a position of the slide is provided.

4. The syringe pump according to claim 3, wherein the slide is connected via a tube with he syringe holding head, through which tube extends an axially movable rod for adjusting the brake element relatively to the syringe holding head.

5. The syringe pump according to claim 2, wherein said syringe pump additionally comprises a winglike syringe portion and a positioning means engaging the winglike syringe portion, the positioning means being coupled to the syringe holding head such that it presses the winglike syringe portion against a stop wall when the syringe holding head radially approaches an inserted syringe.

6. The syringe pump according to claim 2, wherein a releasable locking means locking the syringe holding head in its position is provided.

7. The syringe pump according to claim 6, wherein the locking means engages a slide.

8. The syringe pump according to claim 6, wherein the locking means comprises a rotatable shaft having a rack-type toothing.

9. The syringe pump according to claim 8, wherein the shaft comprises an opening matching a special wrench for actuating and releasing the locking means.

10. The syringe pump according to claim 1, wherein a linear drive for the brake element extends below the syringe cylinder and an actuating means being arranged on the first side of the syringe and the syringe holding head configured for contacting and holding the syringe cylinder being arranged on the second side of the syringe.

11. A syringe pump comprising a syringe holder for holding a syringe cylinder of a syringe, a drive head for engaging a piston plate of a piston rod of the syringe, the drive head being carried by a drive rod extending parallel to the syringe cylinder when the syringe is positioned in the syringe holder, and a brake element transversely movable to longitudinal direction of the syringe towards the drive rod to engage the piston rod,
    a syringe holding head for pressing the syringe cylinder against a syringe bearing, wherein the brake element is positioned, at least partially, in the syringe holding head.

12. The syringe pump according to claim 11, wherein a linear drive for the brake element extends below the syringe when the syringe is positioned in the syringe holder.

13. The syringe pump according to claim 12, wherein a portion of the syringe holding head engages the syringe cylinder and the brake element engages the piston rod.

14. The syringe pump according to claim 13, wherein the syringe holding head is connected to a handle knob.

15. The syringe pump according to claim 11, wherein a portion of the syringe holding head engages the syringe cylinder and the brake element engages the piston rod when the syringe is positioned in the syringe holder.

16. The syringe pump according to claim 15, wherein a spindle rod projects through the syringe holding head and engages the brake element.

17. The syringe pump according to claim 11, wherein said syringe pump additionally comprises a winglike syringe portion, a positioning means engaging the winglike syringe portion, the positioning means being coupled to the syringe holding head such that it presses the winglike syringe portion against a stop wall when the syringe holding head radially approaches an inserted syringe.

\* \* \* \* \*

UNITED STATES PATENT AND TRADEMARK OFFICE
CERTIFICATE OF CORRECTION

| | |
|---|---|
| PATENT NO. | : 7,422,570 B2 |
| APPLICATION NO. | : 10/346609 |
| DATED | : September 9, 2008 |
| INVENTOR(S) | : Hans-Josef Gerlach et al. |

Page 1 of 1

It is certified that error appears in the above-identified patent and that said Letters Patent is hereby corrected as shown below:

In column 5, line 43, in Claim 4, delete "he" and insert -- the --, therefor.

In column 6, line 23, in Claim 11, after "to" insert -- a --.

Signed and Sealed this

First Day of June, 2010

David J. Kappos
*Director of the United States Patent and Trademark Office*